(12) United States Patent
Clune et al.

(10) Patent No.: US 6,640,348 B1
(45) Date of Patent: Nov. 4, 2003

(54) FORMING CONTINUOUS FASTENER MATERIAL

(75) Inventors: William Clune, Concord, NH (US); George A. Provost, Litchfield, NH (US)

(73) Assignee: Velcro Industries B.V., Curacao (NE)

( * ) Notice: Subject to any disclaimer, the term of this patent is extended or adjusted under 35 U.S.C. 154(b) by 261 days.

(21) Appl. No.: 09/711,227

(22) Filed: Nov. 9, 2000

(51) Int. Cl.[7] .................. A44B 18/00; B29C 53/36; B29C 53/38; B29C 53/58; B32B 3/06

(52) U.S. Cl. .................. 3/203; 156/66; 156/218; 156/244.19; 156/244.25; 156/269; 156/271; 156/244.24; 24/442; 24/452; 264/167; 428/100

(58) Field of Search .................. 156/199, 200, 156/203, 218, 217, 66, 244.19, 244.11, 244.25, 250, 269, 271, 244.24; 139/DIG. 1; 428/99, 100; 24/442, 452, 443–451; 264/167

(56) References Cited

U.S. PATENT DOCUMENTS

| | | | |
|---|---|---|---|
| 2,668,296 A | * | 2/1954 | Welch .................. 156/203 X |
| 3,340,116 A | | 9/1967 | Naito |
| 3,522,637 A | | 8/1970 | Brumlik |
| 3,624,749 A | | 11/1971 | Girard et al. |
| 3,665,584 A | | 5/1972 | Erb |
| 3,735,468 A | | 5/1973 | Erb |
| 4,001,366 A | | 1/1977 | Brumlik |
| 4,647,416 A | | 3/1987 | Seiler, Jr. et al. |
| 4,654,246 A | | 3/1987 | Provost et al. |
| 4,672,722 A | | 6/1987 | Malamed |
| 4,701,361 A | | 10/1987 | Van Erden |
| 4,794,028 A | * | 12/1988 | Fischer .................. 264/167 X |
| 4,808,099 A | | 2/1989 | Van Erden |
| 4,842,907 A | | 6/1989 | Van Erden |
| 4,931,003 A | | 6/1990 | Van Erden |

FOREIGN PATENT DOCUMENTS

| | | | |
|---|---|---|---|
| EP | 0 464 754 A1 | * 1/1992 | |
| JP | 63-308248 A | * 12/1988 | .................. 156/203 |

OTHER PUBLICATIONS

"Fundamentals of Packaging Technology" by Walter Soroka, Institute of Packaging Professionals, Herndon, VA, pp. 487–489, 1999.

* cited by examiner

Primary Examiner—Adrienne C. Johnstone
(74) Attorney, Agent, or Firm—Fish & Richardson P.C.

(57) ABSTRACT

A method of reorienting directional features associated with manufacture of continuous fastener materials to produce products having such reoriented features, produces fastener products having an array of individual fastener elements extending from a sheet-form base, the fastener elements adapted to engage mating elements for releasable fastening. The method includes the steps of forming a continuous pre-form product having a planar base defining longitudinal edges and an array of fastener elements extending from the base; joining the longitudinal edges of the pre-form product to form a tube having a seam defined by the joined longitudinal edges; and severing the tube across the seam to form the fastener product with segments of seam extending between longitudinal edges of the fastener product. Various techniques for performing the method and various products taking unique advantage of these techniques are disclosed for providing novel fastener products.

11 Claims, 9 Drawing Sheets

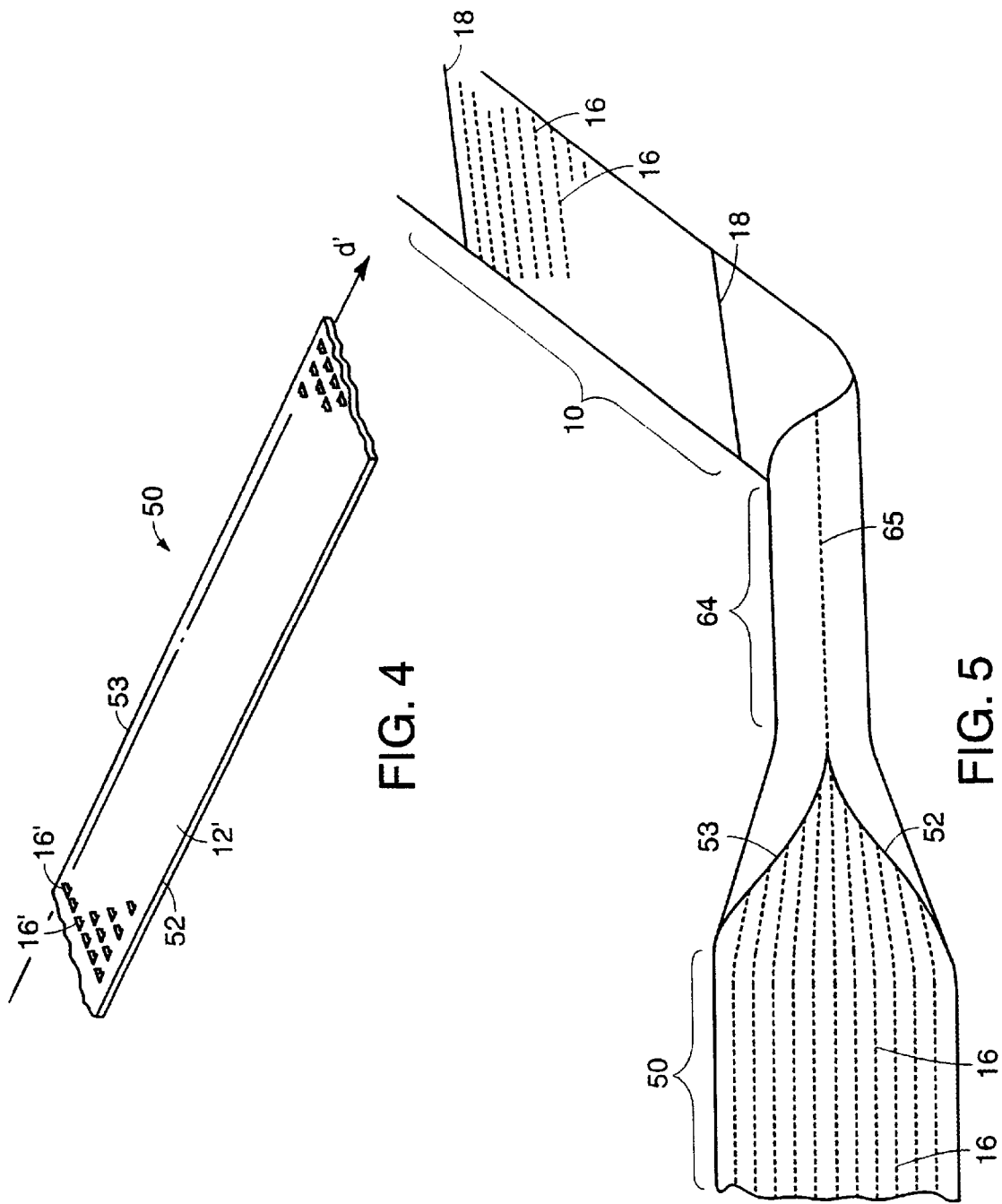

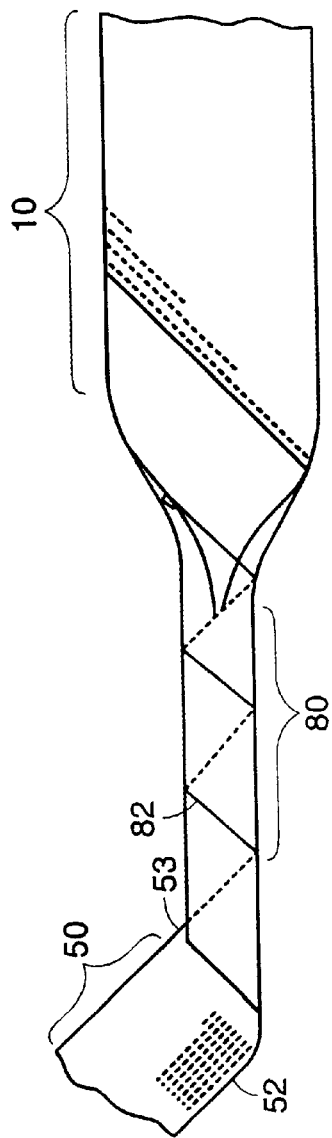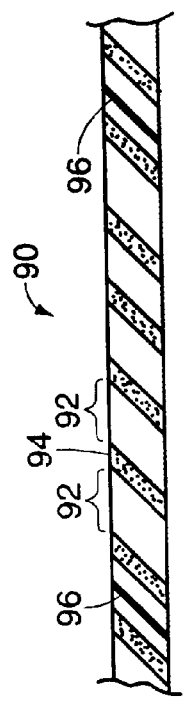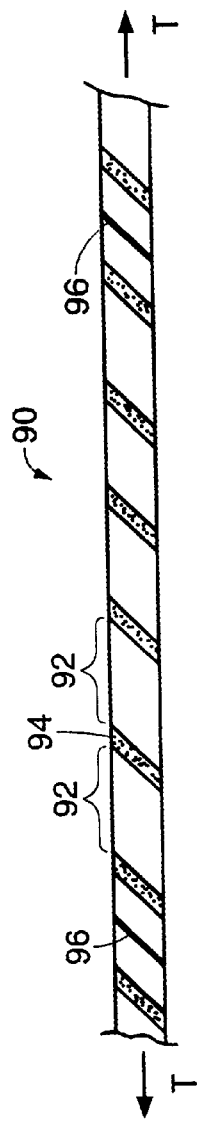

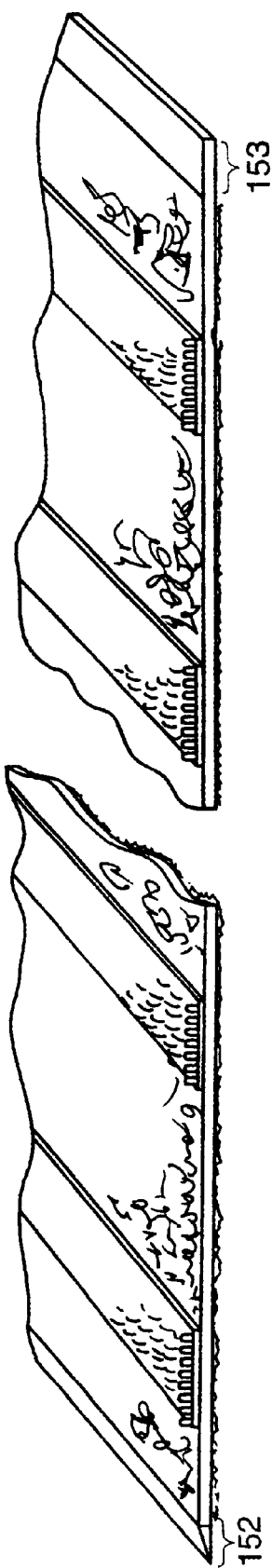
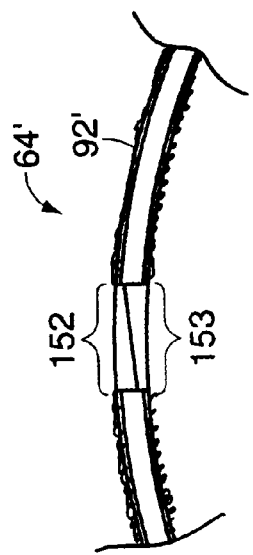
FIG. 9A
FIG. 9B

FORMING CONTINUOUS FASTENER MATERIAL

TECHNICAL FIELD

This invention relates to continuous fastener products and methods and apparatus for forming them.

BACKGROUND

The use of so called "hook and loop" fasteners has become exceedingly prevalent in consumer, industrial and medical applications, and virtually any other situations in which fastening is necessary. Such fastening materials are often advantageously manufactured in continuous strip-form to gain various economies inherent in continuous manufacturing techniques and for convenient shipment and storage in roll form for later use. Methods of continuous manufacture frequently result in continuous fastener products having certain directional characteristics, i.e., features associated with their direction of continuous manufacture ("machine direction") which are distinct from features perpendicular to their direction of continuous manufacture ("cross-machine direction").

While the use of continuously manufactured fastener products is desirable for numerous fastener applications, in some instances the "as-manufactured" direction of the directional features associated with the manufacturing process is less desirable than other possible directional feature orientations. The ability to transform the directional orientation of these directional features to a more desirable direction during continuous manufacture of the fastener product is highly advantageous.

The invention features a novel method of reorienting directional characteristics of a continuously manufactured fastener product to a more desirable direction. The invention also features a novel continuously manufactured fastener product with reoriented directional characteristics.

SUMMARY

In one aspect the invention provides a method of forming a fastener product having an array of individual fastener elements extending from a sheet-form base, the fastener elements adapted to engage mating elements for releasable fastening. The method includes the steps of forming a continuous pre-form product having a planar base defining longitudinal edges and an array of fastener elements extending from the base; joining the longitudinal edges of the pre-form product to form a tube having a seam defined by the joined longitudinal edges; and severing the tube across the seam to form the fastener product with segments of seam extending between longitudinal edges of the fastener product.

Variations of this aspect of the invention may include one or more of the following additional features. The step of forming the pre-form product includes continuously extruding resin and continuously molding the resin to form the array of fastener elements integrally with a surface of the pre-form product. The fastener elements of the pre-form product are molded fastener elements overhanging the base to define an overhang direction, the overhang direction in the fastener product extending at least obliquely toward one of the longitudinal edges of the fastener product. The overhang direction of the molded fastener elements in the fastener product extend perpendicular to the longitudinal edges of the fastener product. The base of the pre-form product has a widthwise elastic region corresponding to a longitudinally elastic region in the fastener product. The step of forming the pre-form product includes introducing a sheet-form, uni-directionally elastic material to a pressure gap defined against a rotating mold roll, the uni-directionally elastic material having widthwise elasticity and being longitudinally inelastic to form the widthwise elastic region of the base of the pre-form product corresponding to the longitudinally elastic region in the fastener product. The uni-directionally elastic material includes at least one surface of exposed loop material engageable by the fastener elements. The base of the fastener product is resiliently elastic within its plane. The fastener elements are hook-shaped. The step of severing comprises severing the tube to form a sheet-form fastener product, then slitting the sheet-form fastener product to form multiple continuous strips of fastener product. The step of severing comprises severing the tube along a helical path. The step of joining comprises wrapping the pre-form product to form a tube with opposite longitudinal edges of the pre-form product joined to form a helical seam about the tube; the step of severing including severing the tube along a longitudinal path to form the fastener product. The step of forming the pre-form product further includes shaping selvedge portions along the longitudinal edges of the pre-form product to facilitate joining the longitudinal edges to form the tube.

In another aspect, the invention provides a method of forming a strip-form fastener product having an array of individual fastener elements extending from a continuous base with the fastener elements being adapted to engage mating elements for releasable fastening. The method includes the steps of molding a continuous pre-form product having a planar base and an array of fastener elements extending from the base, the fastener elements overhanging the base to define an overhang direction; joining the longitudinal edges of the pre-form product to form a tube; and severing the tube to form the strip-form fastener product with the overhang direction of the fastener elements extending toward a longitudinal edge of the strip-form fastener product.

Variations on this aspect of the invention may include one or more of the following features. The step of severing includes severing the tube along a helical path. The step of joining includes wrapping the pre-form product to form a tube with opposite longitudinal edges of the pre-form product joined to form a helical seam about the tube; the step of severing comprising severing the tube along a longitudinal path to form the fastener product.

In another aspect, the invention provides a continuous strip-form fastener product of finite width and having two longitudinal edges, the product including a series of joined pre-form tape segments, each having a planar base with opposite machine direction edges extending between longitudinal edges of the product, and an array of fastener elements extending from the base and arranged in rows parallel to the machine direction edges, adjacent tape segments permanently joined along seams at their machine direction edges.

Variations on this aspect of the invention may include one or more of the following additional features. The array of fastener elements includes rows of molded hooks, each hook having a head overhanging the base in a direction parallel to the machine direction edges of the pre-form tape segments and a direction extending toward a longitudinal edge of the fastener product. The pre-form tape segments further include elastic zones having resiliency in a direction transverse to the machine direction edges of the pre-form tape, the elastic zones forming zones of increased longitudinal elasticity in the strip-form fastener product. At least one-surface of the elastic zones includes a loop material engageable by the fastener elements.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a view similar to that of FIG. 1 illustrating a pre-form product for producing the fastener of FIG. 1.

FIG. 5 illustrates the pre-form product of FIG. 4 being processed to form the fastener product of FIG. 1.

FIG. 6 is a view similar to that of FIG. 5 illustrating an alternative method of forming the fastener product of FIG. 1 from the fastener product of FIG. 4.

FIG. 7 illustrates an alternative embodiment of a continuous strip of fastener product of the invention.

FIG. 7A illustrates the fastener product of FIG. 7 in a stretched condition.

FIG. 9A is a view taken from the direction of line 9A—9A of FIG. 9.

FIG. 9B illustrates marginal edge portions of a cross-section of the pre-form product of FIG. 9 during processing to form the fastener product of FIG. 7.

Like reference symbols in the various drawings indicate like elements.

DETAILED DESCRIPTION

Figure 1:
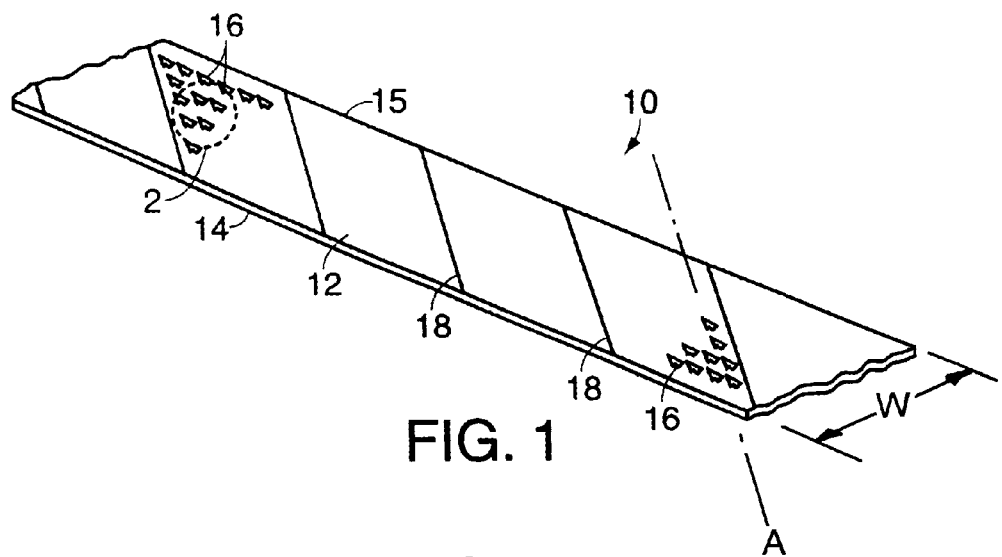
FIG. 1 illustrates a continuous strip of fastener product of the invention.

FIG. 1 illustrates a continuous strip of fastener product 10 having a flexible planar base 12 defining opposite longitudinal edges 14, 15 along its width "w". A multitude of fastener protrusions, e.g., hook-like elements 16, arranged in parallel rows protrude from base 12 and equally spaced seams 18 traverse the width of base 12 in a direction parallel that of the hook rows, i.e., along line A. Hooks 16 are formed integrally from the same material as plastic base strip 12 as described below.

Figure 2:
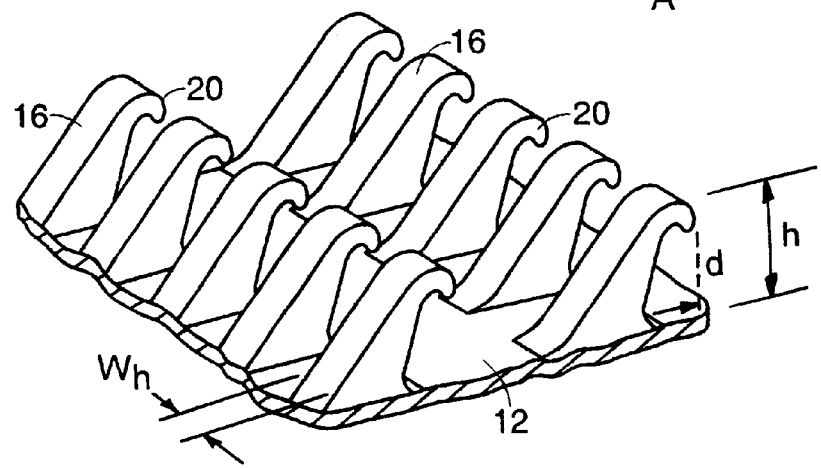
FIG. 2 is an enlarged view of the area indicated by Circle 2 of FIG. 1.

Referring now also to FIG. 2, hooks 16 project from base 12 and are equipped with a crook 20 for engaging mating fastener material, e.g., hook-engageable loop material. Each crook 20 projects out from a stem 22 to define an overhang direction (arrow d in FIG. 2) relative to base 12, the direction of overhang being parallel to the rows of hooks 16. A suitable shape for hooks 16 is, for example, of CFM-29 designation, available from Velcro USA Inc. of Manchester, N.H. The CFM-29 hooks are only 0.015 inch (0.38 mm) in height h, with a width $w_h$ of 0.017 inch. The thickness of the base material is 0.005. Alternative protrusion shapes, such as mushrooms, palm trees, flat-topped hooks, or other loop-engageable shapes are also suitable.

Figure 2A:
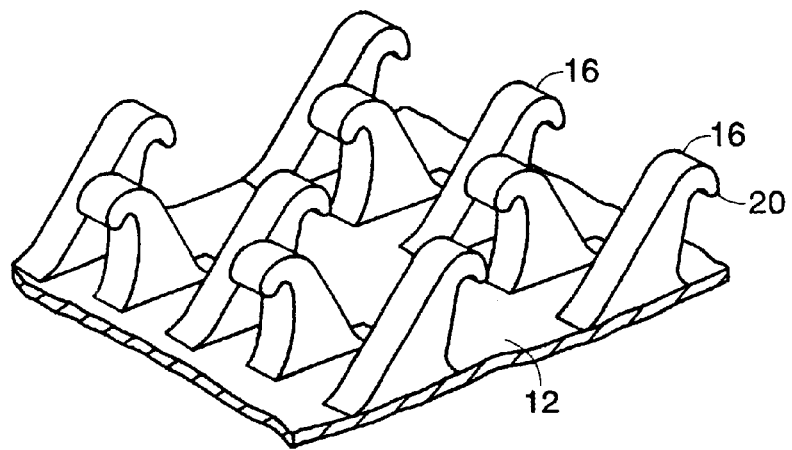
FIG. 2A is a view similar to that of FIG. 2 illustrating an alternative hook arrangement.

FIG. 2A illustrates an alternative, currently preferred, arrangement of hooks 16 having hooks of alternate rows overhanging base 12 in opposite, parallel directions (as indicated by arrows d, d').

Figure 3:
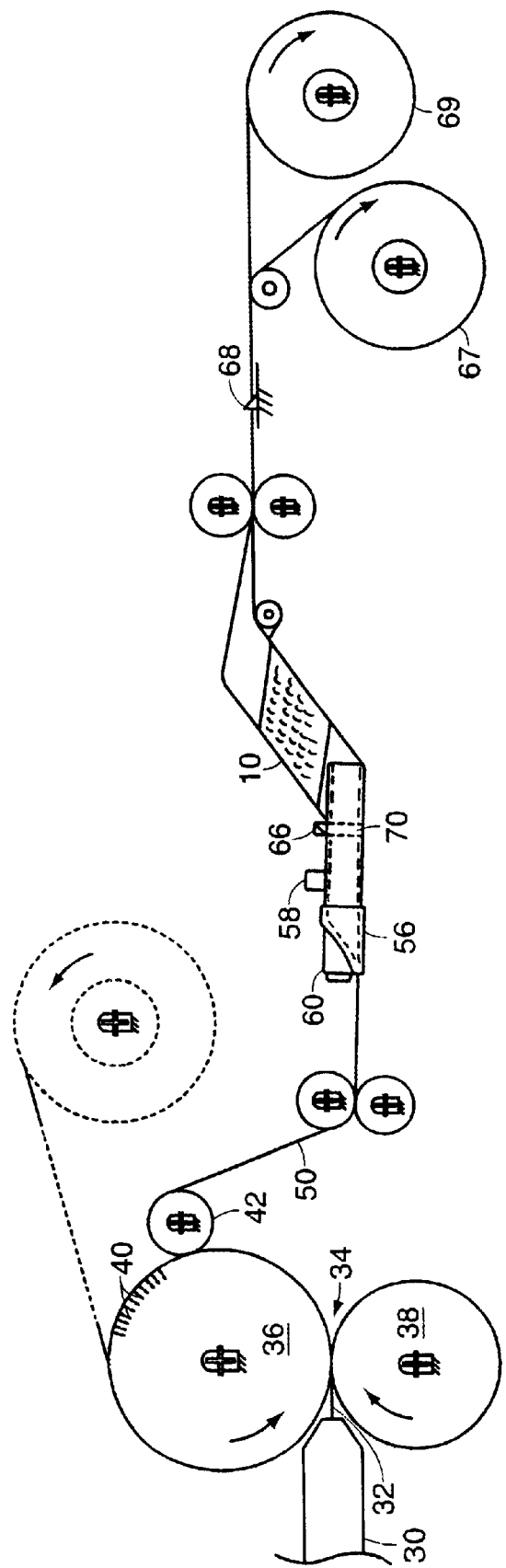
FIG. 3 is a diagrammatic illustration of a method and apparatus for producing the fastener product of FIG. 1.

FIG. 3 illustrates a method and apparatus for producing the above described fastener product. The method builds upon the continuous extrusion/roll-forming method for molding fastener elements on an integral, sheet-form base described by Fischer in U.S. Pat. No. 4,794,028, the contents of which are hereby incorporated by reference. The relative position and size of the rolls and other components are not to scale. An extrusion head 30 supplies a continuous sheet of molten resin 32 to a nip 34 between a rotating mold roll 36 and a counter-rotating pressure roll 38. Mold roll 36 contains an array of miniature, fastener element-shaped mold cavities extending inward from its periphery for molding the fastener protrusions, e.g. hooks 16 (FIGS. 1, 2). Pressure in nip 34 forces resin into the fastener element cavities and shapes the resin to form the substrate (base 12 in FIG. 1). The formed product is cooled on the mold roll until the solidified fastener elements (e.g., hooks 16) are stripped from their fixed cavities by a stripper roll 42.

Referring now also to FIG. 4, the product 50 that is stripped from the mold roll 36 is the pre-form product for use in making the above described fastener product 10 through processing further described below. Pre-form product 50 includes both fastener elements 16' and base 12' and is a seamless continuous strip of fastener tape having parallel opposite longitudinal edges 52, 53 that are formed in a direction tangential to nip rolls 36, 38. This tangential direction is also known as the machine direction of the pre-form process. Crooks 22 of hooks 16 overhang base 12 in a direction (arrow d in FIG. 2) parallel to the machine direction.

Referring again to FIG. 3, pre-form product 50 proceeds from stripper roll 42 to a stationary mandrel 60. Folding plate 56 wraps pre-form product 50 in a width-wise manner about mandrel 60 bringing longitudinal edges 52, 53 to an overlapping or adjacent position. Joining apparatus 58 then joins longitudinal edges 52, 53, e.g., by heat staking, adhesive, ultrasonic bonding, or any other known method of bonding plastics, to form a tubular fastener product 64 (see FIG. 5) having a seam 65 formed at the joined longitudinal edges. Mandrel 60 typically has a circumference slightly smaller than the width of pre-form product 50 so that wrapping of pre-form product 50 about the mandrel allows some overlap of longitudinal edges 52, 53. Alternatively, mandrel 60 has a circumference slightly greater than the width of pre-form product 50 and another material, e.g., hot-melt adhesive, is introduced between the edges to accomplish the joining and form seam 65 (FIG. 5).

Located on mandrel 60 at a position downstream from the longitudinal edge joining apparatus 58 is a rotating collar 70 which is equipped with a bias cutter 66. As the tubular product passes over rotating collar 70, bias cutter 66 cuts the tubular product continuously on the bias to convert the tubular product into ribbon form 10. The resulting fastener product 10 is then stripped from mandrel 60 and wound into a continuous roll of fastener product or is further split by a cutter 68 into multiple fastener tape products (2 fastener tape product rolls, 67, 69 are shown in FIG. 3, but additional splitting may be performed as desired).

The resulting fastener product 10 has all of the features discussed above in reference to FIG. 1. The above described process transforms machine direction longitudinal edges 52, 53 of pre-form product 50 into transverse seams 18 and provides fastener product 10 having a crook overhang direction (arrow d in FIG. 2) parallel to seams 18, i.e., the crooks overhang base 12 in a direction transverse to longitudinal fastener tape edges 14, 15.

FIG. 6 illustrates an alternative process for transforming pre-form product 50 to product fastener tape 10. Again referring also to FIG. 3, to transform pre-form product 50 as illustrated in FIG. 6, stationary mandrel 60 is replaced with a rotating mandrel (not shown). As pre-form product 50 is introduced onto the rotating mandrel, the rate of mandrel rotation is coordinated with the feed speed of pre-form product 50 and its approach angle to rotating mandrel 60 so that pre-form product 50 is wrapped about the rotating mandrel with longitudinal edges 52, 53 in adjacent wraps either overlapped or slightly spaced adjacently as described above. Joining apparatus 58 is positioned on the bias to bond overlapped or adjacent longitudinal edges as the mandrel turns to form a spiral seam 82 along the resulting tubular fastener product 80. Tubular fastener product 80 exits mandrel 60 and is straight-cut by a stationary cutter along a line parallel to the central axis of tubular fastener product 80 to form fastener tape 10.

In another embodiment, illustrated in FIG. 7, a fastener product 90 similar to that of FIG. 1 is formed having stretchy zones 92 of a relatively elastic material interposed between relatively inelastic bands 94 of rows of fastener elements, e.g., hooks 16 of FIGS. 1 and 2. For ease of manufacturing, as further described below, the elasticity of the material of zones 92 is limited to a direction orthogonal to seams 96 and the material is relatively inelastic in a direction parallel to seams 96. The resulting fastener product 90 has a degree of longitudinal stretchiness, i.e., fastener product 90, in relaxed condition (FIG. 7), has inelastic bands 94 of rows of fastener elements of width $w_h$ and stretchy zones 92 of width $w_s$ and in tension (arrows T, FIG. 7A) inelastic bands 94 of rows of fastener elements remain of width $w_h$ while stretchy zones 92 have increased width $w_{s1}$.

Figure 8:
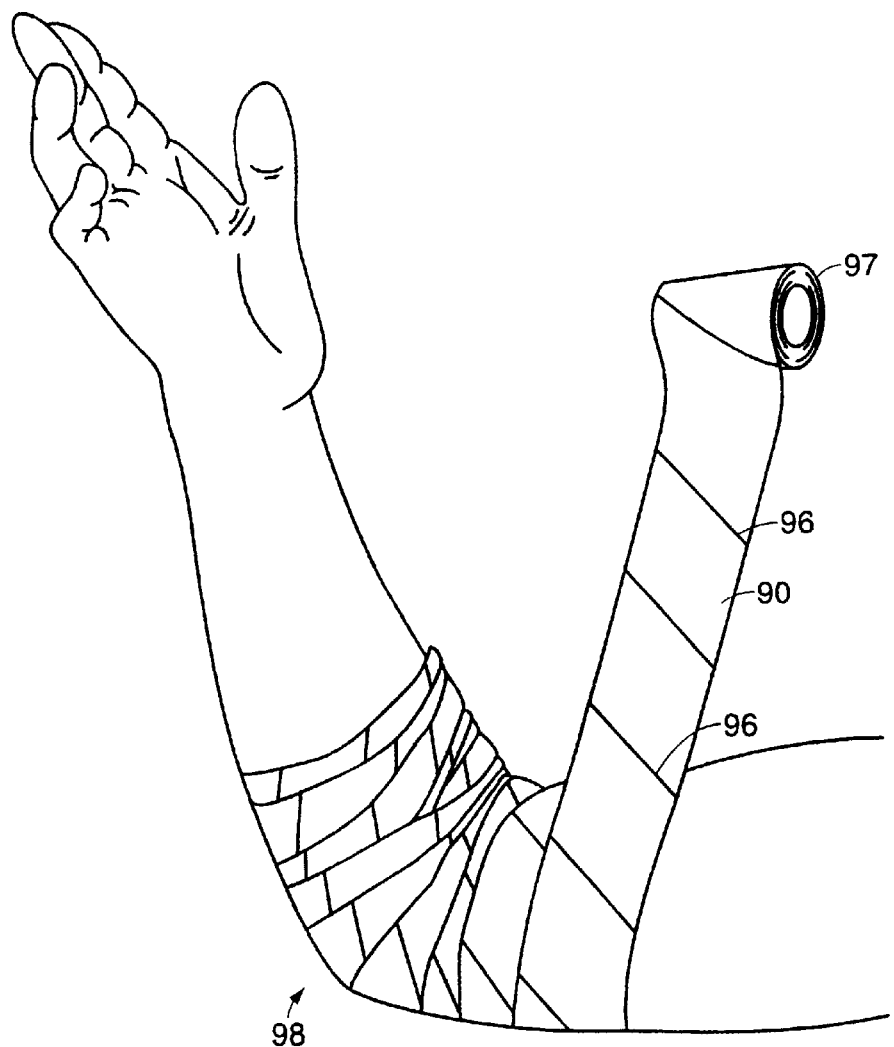
FIG. 8 illustrates an application of the fastener product of FIG. 7.

In one particularly important example of the embodiment of FIG. 7, uni-directionally stretchy material of zones 92 has at least its surface opposite the bands of hooks comprised of a hook-engageable loop material engageable by fastener elements, e.g., hooks of bands 94. As illustrated in FIG. 8, this allows the fastener tape 90 to be pulled from a continuous roll 97, stretched, wrapped, and continuously fastened to itself in its stretched condition about, for example, a human joint, e.g., elbow 98, to support the joint. The fastener tape can then be cut to a desired length.

Fastener product 90 is formed by a modification of the above-described process in which the material of elastic zones 92 is laminated to bands 94 of rows of hooks. In one example, the modified process builds upon the continuous extrusion/roll-forming method for molding fastener elements on an integral, sheet-form base of previously incorporated U.S. Pat. No. 4,794,028, and the nip lamination process described by Kennedy et al. in U.S. Pat. No. 5,260,015, the contents of which are hereby incorporated by reference.

Figure 9:
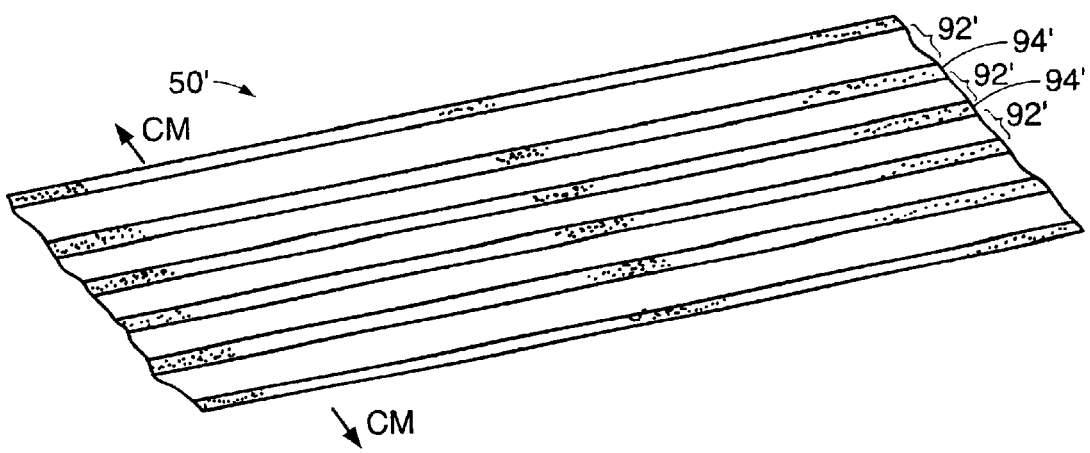
FIG. 9 illustrates a pre-form product for producing the fastener product of FIG. 7.

Referring to FIG. 9, pre-form product 50' is produced having a multiplicity of spaced narrow longitudinal (machine direction) bands 92' of fastener hooks, similar to those described above, on a base of uni-directionally stretchy loop material 94'. Bands of stretchy loop material are exposed between the spaced bands 92' of fastener hooks. Pre-form product 50' presents a striped appearance sometimes referred to here as a "zebra-like" appearance.

For further details of producing such "zebra-like" products and materials, processes, and apparatus for making such products, the reader is referred to U.S. patent application Ser. No. 60/242,877, to Krantz et al., entitled "Hook and Loop Fastening", and filed Oct. 24, 2000 (published as a utility application on Feb. 21, 2002 as Publ. No. US-2002-0022108-A1), the entire contents of which are hereby incorporated by reference.

One such "zebra-like" product, illustrated in FIGS. 9 and 9A, made by modifications to the process described above with reference to FIG. 3. As more fully described in the above incorporated references, pre-form product 50' (FIGS. 9, 9A) is formed by an in situ lamination process in which molten resin 32 is extruded through nip 34. However, in this embodiment, extruder head 30 is equipped with a slot-form die (not shown) to provide molten resin 32 in multiple narrow bands spaced at predetermined intervals across the width of nip 34. Mold roll 36 has fastener element-shaped mold cavities in regions corresponding to the narrow bands of resin. As indicated by dashed lines, uni-directionally stretchy (i.e., stretchy only in the cross-machine direction as indicated by arrows CM in FIG. 9) loop material 92' is simultaneously fed into nip 34 and is at least partially penetrated by the bands of resin 32 while the bands 94' of resin are also molded to have fastener elements 16 extending from a surface to in situ laminate bands 92' of fastener elements to loop material 92'.

The relative inelasticity of loop material 92' in the machine direction advantageously allows suitable machine direction tension to be maintained on the material to ensure that it tracks well to the machine, and can be removed from the machine without undue concern as to the complete solidification of the resin, or risk that the web will wander from its desired track or wrinkle or otherwise distort.

Pre-form product 50' is removed from mold roll 36 by stripper roll 42 and is then formed into a tube, welded, and cut into strips of desired width in a process similar to those described above with reference to FIGS. 5 and 6. The resulting fastener product 90 (FIG. 7) has a degree of longitudinal stretchiness due to the transformation of seamless, width-wise stretchy, pre-form product 50' into a continuous series of bonded transverse bands of fastener material that is stretchy in a direction orthogonal to seams 96.

Referring now to FIGS. 9A and 9B, pre-form product 50' (or pre-form product 50 of FIG. 4) advantageously has selvedge portions 152, 153 along longitudinal edges 52', 53' formed of thermoplastic resin. Thermoplastic selvedge portions 152, 153 facilitate joining longitudinal edges 52', 53' by e.g., thermobonding, during formation of the tubular fastener product 64' (FIG. 9B) from which fastener product 90 is cut, as in the above described process. Selvedge portions 152, 153 have tapered surfaces 154, 155, respectively, that allow the longitudinal edges to have an overlapped thickness, t, (FIG. 9B) that differs insubstantially from the thickness of the base of fastener product 90 so that the profile of seams 96 is minimized. Additionally, thermoplastic selvedge portions 152, 153 can be shaped to form, e.g., tongue in groove, dovetail, or other mating arrangements, to aid in alignment of longitudinal edges 152, 153 during the joining of longitudinal edges.

Selvedge portions 152, 153 can be formed by modifying the above described process to provide extruded strips of resin 32 along longitudinal edges of loop material 92' as it is fed through nip 34 so that the resin strips at least partially penetrate and bond to loop material 92'. The resin strips are formed into selvedge portions 152, 153 of desired shape by providing corresponding appropriately shaped portions of mold roll 36 and pressure roll 38.

Figure 10:
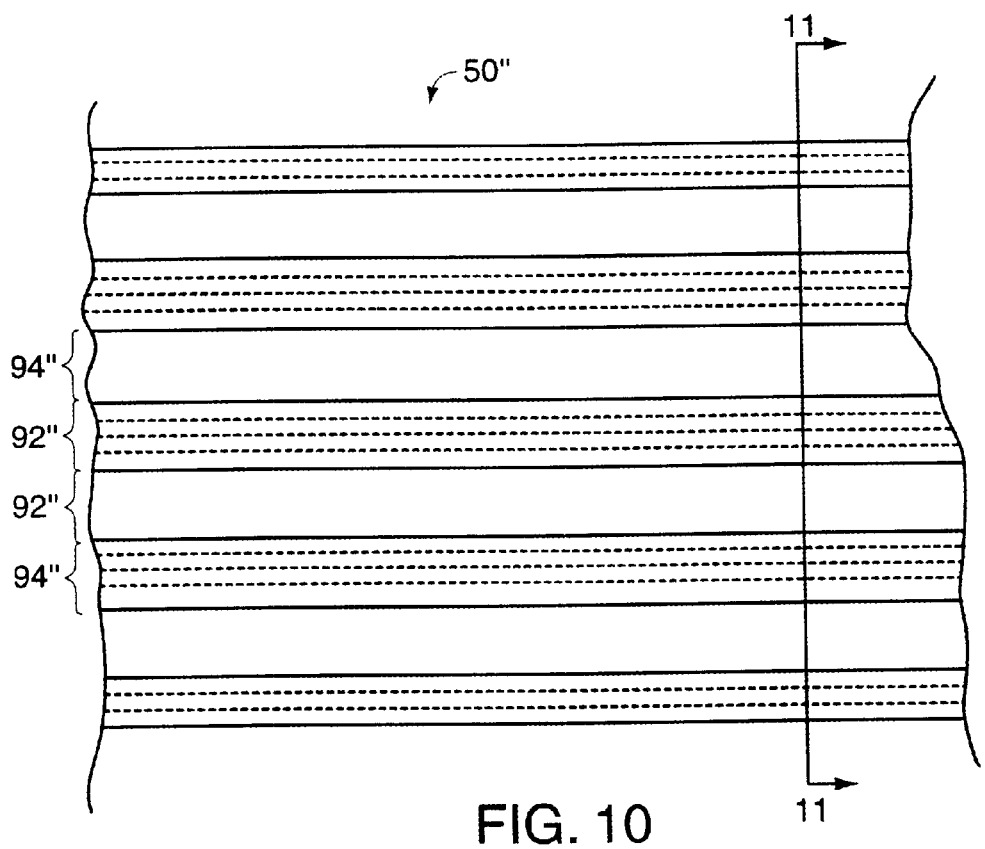
FIG. 10 illustrates a pre-form product for producing the fastener product of FIG. 12.
Figure 11:
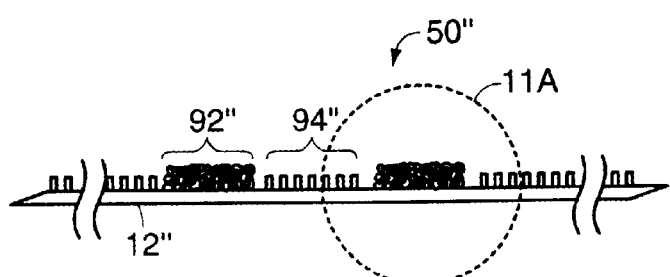
FIG. 11 is a view taken along line 11—11 of FIG. 10.
Figure 12:
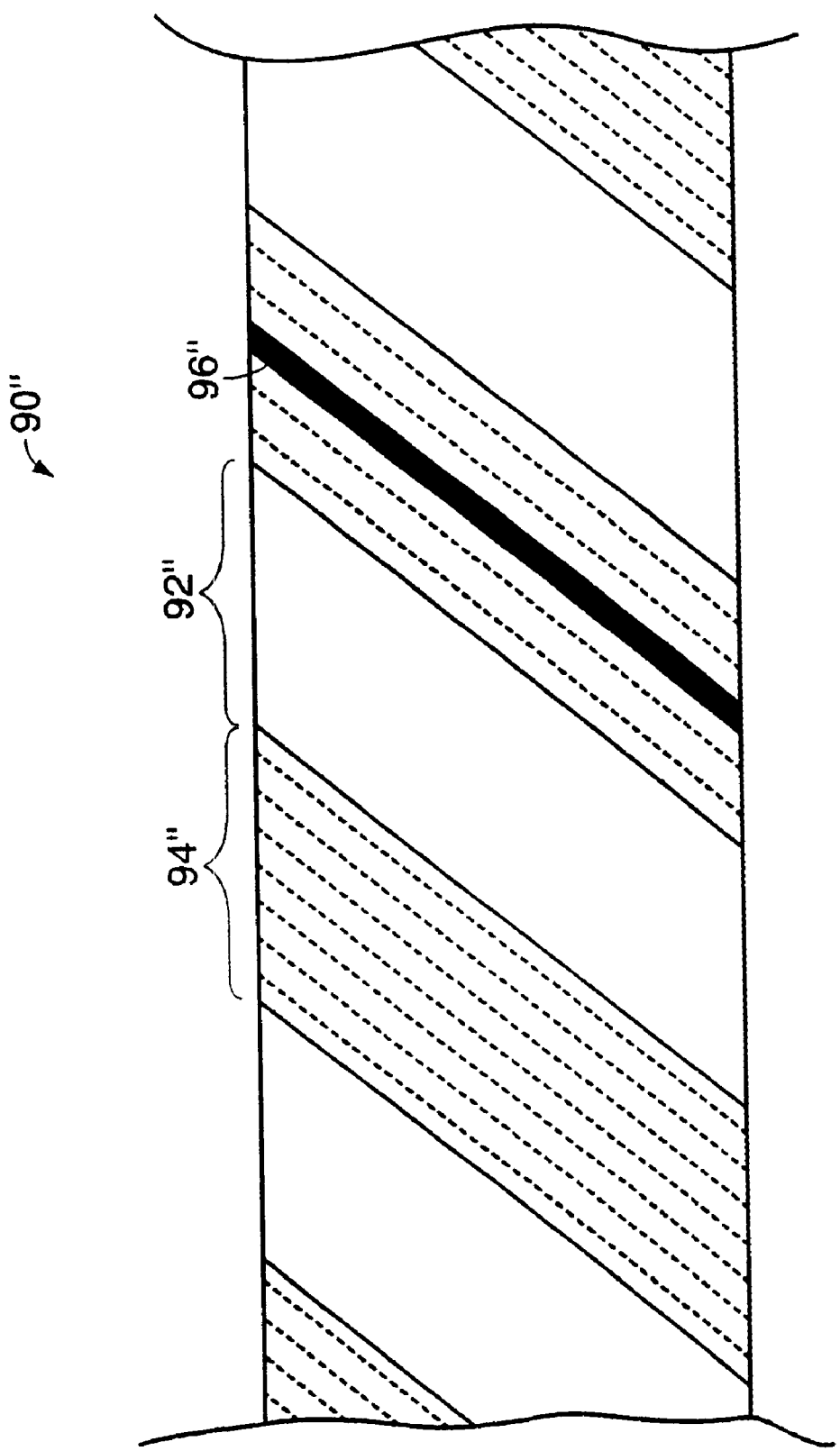
FIG. 12 illustrates an alternative continuous fastener product of the invention.

In another embodiment, illustrated in FIGS. 10–12, a "zebra-like" pre-form product 50" is produced having a multiplicity of alternating narrow longitudinal (machine direction) bands 94" of fastener hooks and narrow longitudinal bands 92" of fastener hook-engageable loop material. Both the fastener hook bands 94" and the fastener hook-engageable bands are exposed on the same surface of pre-form product 50". The underlying base 12" of pre-form product 50" and the bands 94" of fastener hooks are of the same relatively inelastic material.

Figure 11A:
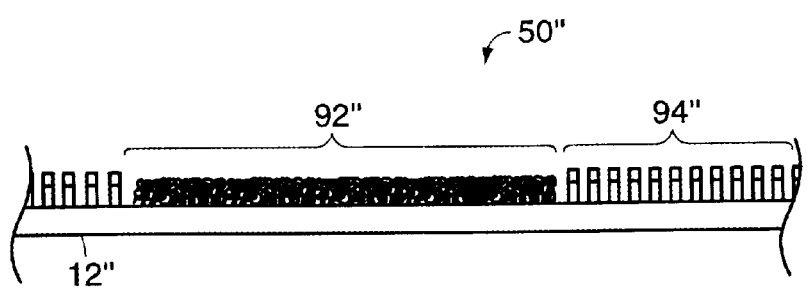
FIG. 11A is a highly enlarged view of the area indicated by circle 11A of FIG. 11.

Pre-form product 50" is made by another modification to the above described process wherein, referring again to FIG. 3, a single band of resin 32 sufficient to form the entire base of pre-form 50" is fed into nip 34 simultaneously with narrow bands 92" of loop material (a single band of such loop material is represented by dashed lines in FIG. 3) spaced at desired intervals. Mold roll 36 has spacer rolls to accommodate bands of loop material 92" with adjacent bands of rows of hook cavities to form bands 94" of fastener hooks. As the bands of loop material are fed through the nip, they are in situ laminated to the base and hook band forming resin, i.e., the loop bands are at least partially penetrated by the molten resin as described above and illustrated in FIGS. 11, 11A, to be permanently bonded to the base 12".

Figure 13:
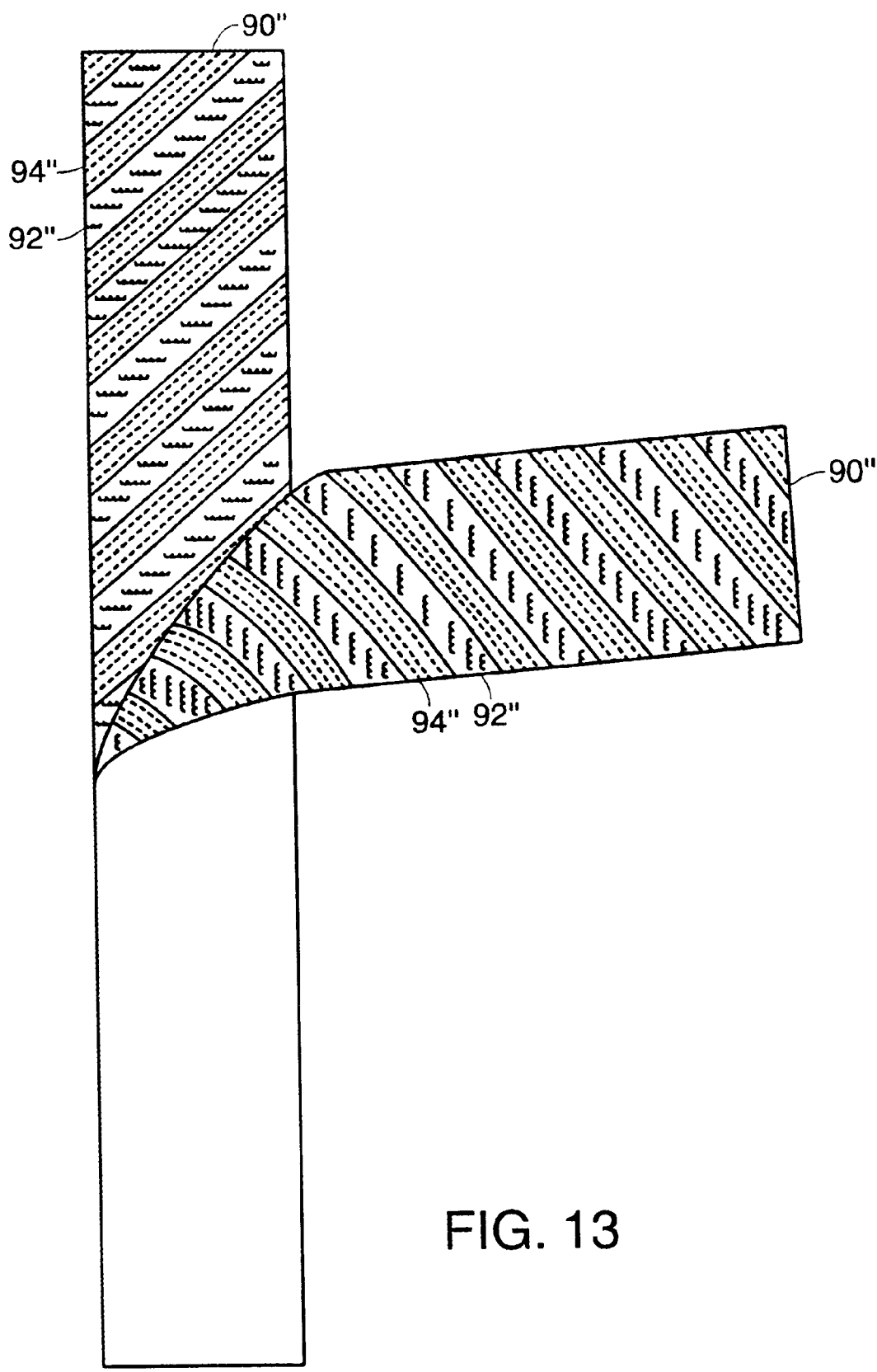
FIG. 13 illustrates strips of the fastener product of FIG. 12 partially fastened to each other.

Subsequently, pre-form product 50" can be helically converted, as described above with reference to FIGS. 3, 5, and 6, to form the fastener product 90" illustrated in FIG. 12 having a series of seams 96" parallel to alternating angled bands 94", 92" of hook and loop fasteners. Such a fastener product can be self-engaged, as illustrated in FIG. 13, by exposing hook and loop band bearing surfaces of the product 90" for face-to-face contact. Through the helical conversion process described above, the bands of hook and loop are angled to allow opposing fastener portions to be presented for fastening with opposite angular orientations of the hook and loop bands (as shown in FIG. 13). This opposite angular orientation avoids a potential failure of opposing fastener portions, e.g., of fastening material that has not been helically transformed as described herein, to fasten caused by loop band to loop band and hook band to hook band alignment of opposing fastener portions, i.e., the opposite angular orientation of the bands ensures contact of a portion of a loop band of one opposing fastener portion with a portion of a hook band of another opposing fastener portion to achieve fastening.

A number of embodiments of the invention have been described. Nevertheless, it will be understood that various modifications may be made without departing from the spirit and scope of the invention. Accordingly, other embodiments are within the scope of the following claims.

What is claimed is:

1. A method of forming a fastener product having an array of individual fastener elements extending from a sheet-form base, the fastener elements adapted to engage mating elements for releasable fastening, the method comprising:

continuously extruding resin and continuously molding the resin to form a continuous pre-form product having a planar base defining longitudinal edges and an array of fastener elements extending integrally from the base;

joining the longitudinal edges of the pre-form product to form a tube having a seam defined by the joined longitudinal edges; and severing the tube across said seam to form the fastener product with segments of seam extending between longitudinal edges of the fastener product.

2. The method of claim 1 wherein the fastener elements of the pre-form product comprise molded fastener elements overhanging the base to define an overhang direction, the overhang direction in the fastener product extending at least obliquely toward one of the longitudinal edges of the fastener product.

3. The method of claim 2 wherein the overhang direction of the molded fastener elements in the fastener product extend perpendicular to the longitudinal edges of the fastener product.

4. The method of claim 1 wherein the fastener elements are hook-shaped.

5. The method of claim 1 wherein the step of severing comprises severing the tube to form a sheet-form fastener product, then slitting the sheet-form fastener product to form multiple continuous strips of fastener product.

6. The method of claim 1 wherein the step of severing comprises severing the tube along a helical path.

7. The method of claim 1 wherein the step of joining comprises wrapping the pre-form product to form a tube with opposite longitudinal edges of the pre-form product joined to form a helical seam about the tube; the step of severing comprising severing the tube along a longitudinal path to form said fastener product.

8. The method of claim 1 wherein the step of forming the pre-form product further comprises shaping selvedge portions along the longitudinal edges of the pre-form product to facilitate joining the longitudinal edges to form the tube.

9. A method of forming a strip-form fastener product having an array of individual fastener elements extending from a continuous base, the fastener elements adapted to engage mating elements for releasable fastening, the method comprising the steps of:

molding a continuous pre-form product having a planar base and an array of fastener elements extending from the base, the fastener elements overhanging the base to define an overhang direction;

joining the longitudinal edges of the pre-form product to form a tube; and severing the tube to form the strip-form fastener product with the overhang direction of the fastener elements extending toward a longitudinal edge of the strip-form fastener product.

10. The method of claim 9 wherein the step of severing comprises severing the tube along a helical path.

11. The method of claim 9 wherein the step of joining comprises wrapping the preform product to form a tube with opposite longitudinal edges of the preform product joined to form a helical seam about the tube; the step of severing comprising severing the tube along a longitudinal path to form said fastener product.

* * * * *